(12) United States Patent
Hallett et al.

(10) Patent No.: US 6,723,735 B1
(45) Date of Patent: Apr. 20, 2004

(54) IMIDAZO-PYRIDINE DERIVATIVES AS LIGANDS FOR GABA RECEPTORS

(75) Inventors: David James Hallett, Watford (GB); Michael Rowley, Rome (IT)

(73) Assignee: Merck Sharp & Dohme Ltd., Hoddesdon ( * ) Notice: Subject to any disclaimer, the term of this patent is extended or adjusted under 35 U.S.C. 154(b) by 21 days.

(21) Appl. No.: 10/070,026

(22) PCT Filed: Aug. 30, 2000

(86) PCT No.: PCT/GB00/03350

§ 371 (c)(1), (2), (4) Date: Feb. 25, 2002

(87) PCT Pub. No.: WO01/18000

PCT Pub. Date: Mar. 15, 2001

(30) Foreign Application Priority Data

Sep. 7, 1999 (GB) ............................................. 9921150

(51) Int. Cl.$^7$ ...................... A61K 31/44; C07D 515/02; A61P 25/00
(52) U.S. Cl. ........................................ 514/303; 546/118
(58) Field of Search ........................... 546/118; 514/303

(56) References Cited

FOREIGN PATENT DOCUMENTS

| EP | 0 563 001 | 9/1993 |
|---|---|---|
| EP | 0 616 807 | 9/1994 |
| WO | WO 98/34923 | 8/1998 |

*Primary Examiner*—Robert W. Ramsuer
*Assistant Examiner*—Robert Shiao
(74) *Attorney, Agent, or Firm*—J. Eric Thies; Melvin Winokur

(57) ABSTRACT

The present invention is directed to 3-phenylimidazol[4,5-b]pyridine derivatives, that are selective ligands for GABA$_A$ receptors. These compounds are useful in the treatment and prevention of disorders of the central nervous system, including anxiety and convulsions.

10 Claims, No Drawings

IMIDAZO-PYRIDINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB00/03350, filed Aug. 30, 2000, which claims priority under 35 U.S.C. § 119 from GB Application No. 9921150.0, filed Sep. 7, 1999.

The present invention relates to a class of substituted imidazo-pyridine derivatives and to their use in therapy. More particularly, this invention is concerned with imidazo[4,5-b]pyridine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta2$ and $\alpha6\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

EP-A-0616807 describes a class of benzimidazole derivatives which are stated to possess potent benzodiazepine receptor affinity, and thus to be useful in the treatment of convulsions, anxiety, sleep disorders, memory disorders and other disorders sensitive to benzodiazepine receptor binding activity. WO 98/34923 relates to a class of 1-phenylbenzimidazole derivatives, substituted at the meta position of the phenyl ring by a methylene-, carbonyl- or thiocarbonyl-linked amine moiety, which are selective ligands for $GABA_A$ receptors and accordingly of benefit in alleviating neurological disorders including anxiety and convulsions. There is, however, no disclosure nor any suggestion in EP-A-0616807 or WO 98/34923 that the benzimidazole nucleus specified therein can be replaced by any other moiety, with in particular no mention being made therein of replacement by the imidazo[4,5-b]pyridine functionality.

EP-A-0563001 describes a class of fused imidazole derivatives which are stated to possess activity as calcium channel blockers. There is, however, no disclosure nor any suggestion in EP-A-0563001 that the compounds described therein might be effective as ligands for $GABA_A$ receptors.

The present invention provides a class of imidazopyridine derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

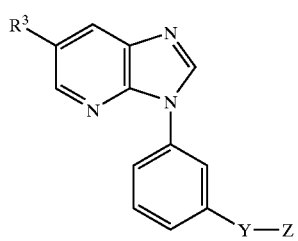

(I)

wherein
Y represents a chemical bond, or a methylene ($CH_2$), carbonyl (C=O), thiocarbonyl (C=S) or amide (CONH or NHCO) linkage;
Z represents an optionally substituted aryl, heteroaryl or heteroaryl($C_{1-6}$)alkyl group, or a group of formula —$NR^1R^2$;

$R^1$ and $R^2$ independently represent hydrogen, hydrocarbon or a heterocyclic group; or $R^1$ and $R^2$, together with the intervening nitrogen atom, represent an optionally substituted heterocyclic ring selected from azetidinyl, pyrrolidinyl, piperidinyl piperazinyl, morpholinyl and thiomorpholinyl; and
$R^3$ represents aryl or heteroaryl, either of which groups may be optionally substituted.

The present invention also provides a compound of formula I as depicted above, or a salt or prodrug thereof, wherein
Z represents an optionally substituted heteroaryl or heteroaryl($C_{1-6}$)alkyl group, or a group of formula —$NR^1R^2$; and
Y, $R^1$, $R^2$ and $R^3$ are as defined above.

Where Z in the compounds of formula I above represents an optionally substituted aryl, heteroaryl or heteroaryl($C_{1-6}$) alkyl group, this group may be unsubstituted, or substituted by one or more, typically one or two, substituents. Suitably, the aryl, heteroaryl or heteroaryl($C_{1-6}$)alkyl group Z is unsubstituted or monosubstituted. Likewise, the aryl or heteroaryl group $R^3$ may be unsubstituted, or substituted by one or more, typically one or two, substituents. Suitably, the group $R^3$ is unsubstituted or monosubstituted. Typical substituents on the groups Z and $R^3$ include $C_{1-6}$ alkyl, halogen, cyano, formyl and $C_{2-6}$ alkylcarbonyl; especially methyl, fluoro, cyano, formyl or acetyl.

Where $R^1$ and $R^2$, together with the intervening nitrogen atom, represent an optionally substituted heterocyclic ring, this ring may be unsubstituted, or substituted by one or more, preferably one or two, substituents. Examples of optional substituents on the heterocyclic ring include $C_{1-6}$ alkyl, hydroxy and oxo. Typical substituents include methyl, hydroxy and oxo.

For use in medicine, the salts of the compounds, of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphony" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, especially phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridaziyl, pyrimidinyl, pyrazinyl, pyranyl, furyl benzofuryl, dibenzofuryl, thienyl, benzthienyl, pyrrolyl, indolyl, pyrazolyl, indazolyl oxazolyl, isoxazolyl, thiazolyl isothiazolyl imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl hydroxy, $C_{1-6}$ alkoxy, aryloxy, oxo, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, formyl, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Typically, Y represents a chemical bond, or a $-CH_2-$ or $-NHCO-$ linkage. In a particular embodiment, Y represents a chemical bond. In another embodiment, Y represents a $-CH_2-$ linkage.

Suitable values for the substituents $R^1$ and $R^2$ include hydrogen, $C_{1-6}$ alkyl, aryl($C_{1-6}$)alkyl and heteroaryl($C_{1-6}$)alkyl, any of which groups may be optionally substituted. Typical substituents include $C_{1-6}$ alyl, $C_{1-6}$ alkoxy and halogen.

Particular values of $R^1$ and $R^2$ include hydrogen, methyl, ethyl and pyridinylmethyl.

Suitably, one of $R^1$ and $R^2$ is other than hydrogen.

Where $R^1$ and $R^2$, together with the intervening nitrogen atom, represent an optionally substituted heterocyclic ring, this ring is suitably a pyrrolidinyl or morpholinyl ring, either of which rings may be unsubstituted or substituted by one or more, preferably one or two, substituents, typically oxo. In this context, typical values for the $-NR^1R^2$ moiety include oxo-pyrrolidinyl and morpholinyl.

Suitably, the substituent Z represents an optionally substituted phenyl, pyridinyl, thienyl or imidazolyl group, or a group of formula $-NR^1R^2$ as defined above. Typical substituents on the moiety Z include cyano, formyl and $C_{2-6}$ alkylcarbonyl, especially cyano, formyl or acetyl.

Illustrative values of Z include cyanophenyl, formylphenyl, acetylphenyl, pyridinyl, cyano-thienyl, imidazolyl, oxo-pyrrolidinyl and morpholinyl.

Representative values for the substituent Z include pyridinyl, imidazolyl, oxo-pyrrolidinyl and morpholinyl.

Suitable values for the substituent $R^3$ include phenyl, furyl and isoxazolyl. Typical values of $R^3$ include phenyl and furyl. A particular value of $R^3$ is furyl.

A particular sub-class of compounds according to the invention is represented by the compounds of formula II, and salts and prodrugs thereof:

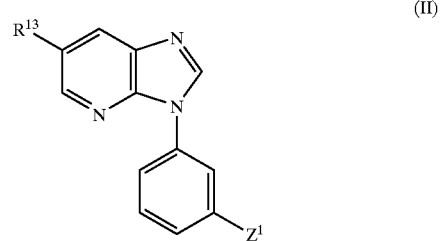

(II)

wherein
  $Z^1$ represents an optionally substituted aryl or heteroaryl group; and
  $R^{13}$ represents phenyl, furyl or isoxazolyl.

The present invention also provides a compound of formula II as depicted above, or a salt or prodrug thereof, wherein
  $Z^1$ represents an optionally substituted heteroaryl group; and
  $R^{13}$ is as defined above.

Suitably, the substituent $Z^1$ is unsubstituted or monosubstituted, typically unsubstituted.

Representative values of $Z^1$ include phenyl, pyridinyl, thienyl and imidazolyl, any of which groups may be optionally substituted by one or more substituents.

Particular values for the substituent $Z^1$ include pyridinyl, thienyl and imidazolyl, any of which groups may be optionally substituted by one or more substituents.

Examples of suitable substituents on the moiety $Z^1$ include $C_{1-6}$ alkyl, halogen, cyano, formyl and $C_{2-6}$ alkylcarbonyl; especially methyl, fluoro, cyano, formyl or acetyl.

Illustrative values of $Z^1$ include cyanophenyl, formylphenyl, acetylphenyl, pyridinyl, cyano-thienyl and imidazolyl.

A specific value of $Z^1$ is pyridinyl. Another value of $Z^1$ is imidazolyl.

Typically, $R^{13}$ represents phenyl or furyl. In one embodiment, $R^{13}$ represents furyl.

Specific compounds within the scope of the present invention include:

6-(furan-3-yl)-3-[3-(pyridin-3-yl)phenyl]-3H-imidazo[4,5-b]pyridine;
1-[3-(6-(furan-3-yl)-3H-imidazo[4,5-b]pyridin-3-yl)phenyl]pyrrolidin-2-one;
6-(furan-3-yl)-3-[3-(imidazol-1-yl)phenyl]-3H-imidazo[4,5-b]pyridine;
6-(furan-3-yl)-3-[3-(morpholin-4-ylmethyl)phenyl]-3H-imidazo[4,5-b]pyridine;
6-phenyl-3-[3-(pyridin-3-yl)phenyl]-3H-imidazo[4,5-b]pyridine;
1-[3'-(6-(furan-3-yl)imidazo[4,5-b]pyridin-3-yl)biphenyl-2-yl]ethanone;
3'-[6-(furan-3-yl)imidazo[4,5-b]pyridin-3-yl]biphenyl-2-carbaldehyde;
3'-[6-(furan-3-yl)imidazo[4,5-b]pyridin-3-yl]biphenyl-2-carbonitrile;
3-[3-(6-(furan-3-yl)imidazo[4,5-b]pyridin-3-yl)phenyl]thiophene-2-carbonitrile;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 50 nM or less, preferably 10 nM or less, and more preferably 5 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk– fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III:

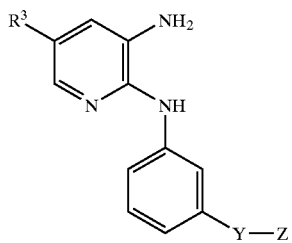

(III)

wherein Y, Z and $R^3$ are as defined above; with formic acid, typically at an elevated temperature, e.g. a temperature in the region of 80–85° C.

The intermediates of formula III may be prepared by reacting a compound of formula IV with a compound of formula V:

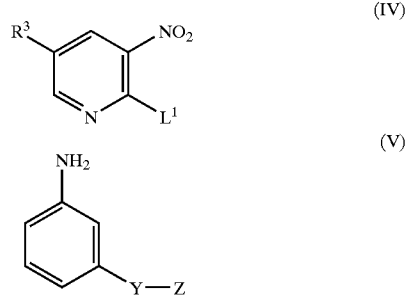

(IV)

(V)

wherein Y, Z and $R^3$ are as defined above, and $L^1$ represents a suitable leaving group; followed by reduction of the nitro group.

The leaving group $L^1$ is suitably a halogen atom, e.g. chloro.

The reaction between compounds IV and V is conveniently carried out under basic conditions, for example in a mixture of 1-methyl-2-pyrrolidinone and triethylamine, or using potassium carbonate in 1,2-dichloroethane or N,N-dimethylformamide, or using triethylamine in dimethylsulphoxide, typically at an elevated temperature.

Reduction of the nitro group in the compound thereby obtained is conveniently effected by treatment with a reducing agent such as sodium sulphide nonahydrate, in which case the reaction is suitably carried out in methanol, typically in the presence of ammonium chloride at the reflux temperature of the solvent.

The compounds in accordance with the present invention in which Y represents a chemical bond may be prepared by a process which comprises reacting a compound of formula VI with a compound of formula VII:

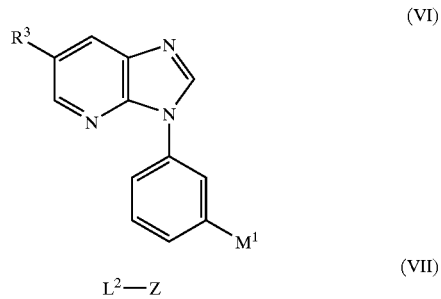

(VI)

(VII)

wherein Z and $R^3$ are as defined above, $L^2$ represents a suitable leaving group, and $M^1$ represents a boronic acid moiety —$B(OH)_2$ or a cyclic ester thereof formed with an organic diol, e.g. pinacol; in the presence of a transition metal catalyst.

The leaving group $L^2$ is typically a halogen atom, e.g. bromo.

The transition metal catalyst of use in the reaction between compounds VI and VII is suitably tetrakis (triphenylphosphine)palladium(0). The reaction is conveniently carried out at an elevated temperature in a solvent such as N,N-dimethylformamide, advantageously in the presence of potassium phosphate.

In another procedure, the compounds according to the present invention in which Y represents a chemical bond may be prepared by a process which comprises reacting a compound of formula VIII with a compound of formula IX:

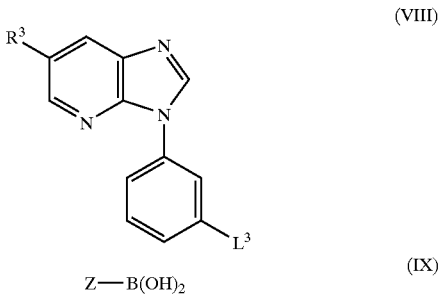

(VIII)

(IX)

wherein Z and $R^3$ are as defined above, and $L^3$ represents a suitable leaving group; in the presence of a transition metal catalyst.

The leaving group $L^3$ is typically trifluoromethanesulphonyloxy.

The transition metal catalyst of use in the reaction between compounds VIII and IX is suitably tris(dibenzylideneacetone)dipalladium(0). The reaction is conveniently carried out at an elevated temperature in a solvent such as N,N-dimethylacetamide, typically in the presence of 2,2'-bis(diphenylphosphino)-1,1'-binaphthyl and potassium phosphate.

Where $M^1$ in the intermediates of formula VI above represents a cyclic ester of a boronic acid moiety —$B(OH)_2$ formed with pinacol, the relevant compound VI may be prepared by reacting bis(pinacolato)diboron with a compound of formula VIII as defined above; in the presence of a transition metal catalyst.

The transition metal catalyst of use in the reaction between bis(pinacolato)diboron and compound VIII is suitably dichloro[1,1'-bis(diphenylphosphino)ferrocene]palladium(II). The reaction is conveniently carried out at an elevated temperature in a solvent such as 1,4-dioxane, typically in the presence of 1,1'-bis(diphenylphosphino)ferrocene and potassium acetate.

In a further procedure, the compounds according to the present invention may be prepared by a process which comprises reacting a compound of formula X with a compound of formula XI:

$$R^3—B(OH)_2 \quad (X)$$

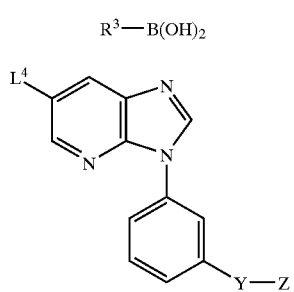

(XI)

wherein Y, Z and $R^3$ are as defined above, and $L^4$ represents a suitable leaving group; in the presence of a transition metal catalyst.

The leaving group $L^4$ is typically a halogen atom, e.g. bromo.

The transition metal catalyst of use in the reaction between compounds X and XI is suitably tetrakis(triphenylphosphine)palladium(0), in which case the reaction is conveniently effected at an elevated temperature in a solvent such as N,N-dimethylformamide or a mixture of 1,3-propanediol and 1,2-dimethoxyethane, typically in the presence of potassium phosphate or sodium carbonate.

Where $L^4$ in the compounds of formula XI above represents a halogen atom, these compounds correspond to compounds of formula I as defined above wherein $R^3$ represents halogen, and they may therefore be prepared by any method analogous to those described above for the preparation of the compounds according to the invention.

Where $L^3$ in the intermediates of formula VIII above represents trifluoromethanesulphonyloxy, the relevant compound VIII may be prepared by reacting the appropriate compound of formula XII:

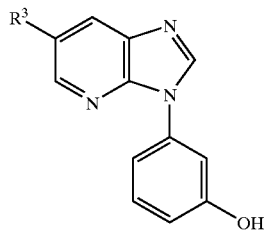

(XII)

wherein $R^3$ is as defined above; with trifluoromethanesulphonic anhydride, typically in the presence of pyridine.

The intermediates of formula XII above may suitably be prepared by reacting a compound of formula X as defined above with a compound of formula XIII:

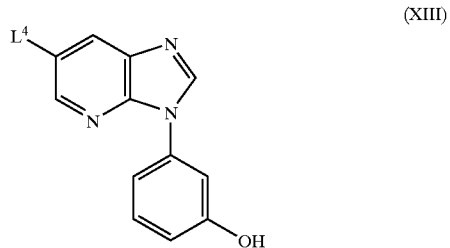

(XIII)

wherein $L^4$ is as defined above; in the presence of a transition metal catalyst; under conditions analogous to those described above for the reaction between compounds X and XI.

The intermediates of formula XIII above may suitably be prepared from the appropriate methoxy-substituted precursor of formula XIV:

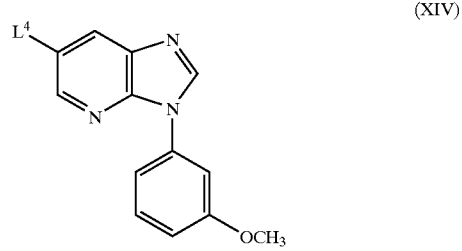

(XIV)

wherein $L^4$ is as defined above; by treatment with hydrobromic acid, typically in acetic acid at an elevated temperature.

The intermediates of formula XIV above may suitably be prepared by reacting a compound of formula XV:

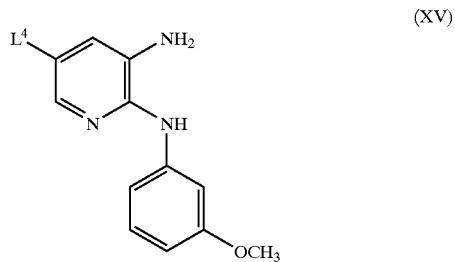

(XV)

wherein $L^4$ is as defined above; with formic acid; under conditions analogous to those described above for the reaction between compound III and formic acid.

The intermediates of formula XV above may suitably be prepared by reacting a compound of formula XVI with the compound of formula XVII:

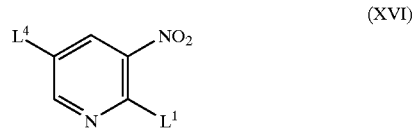

(XVI)

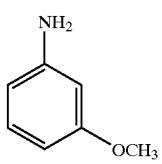
(XVII)

wherein $L^1$ and $L^4$ are as defined above; followed by reduction of the nitro group; under conditions analogous to those described above in relation to the reaction between compounds IV and V.

The intermediate of formula XVIII (m-anisidine) is commercially available, e.g. from Aldrich, Gillingham, United Kingdom.

Where they are not commercially available, the starting materials of formula IV, V, VII, IX, X and XVI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk− cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

6-(Furan-3-yl)-3-[3-(pyridin-3-yl)phenyl]-3H-imidazo[4,5-b]pyridine

2-Amino-5-bromo-3-nitropyridine (21.8 g, 0.1 mol) was ground to a fine powder using a mortar and pestle and then suspended in 6M hydrochloric acid (250 ml). This mixture was cooled to 0° C. and treated with solid $NaNO_2$ (8.3 g, 0.12 mol) at such a rate that the internal temperature remained below 5° C. (ca. 45 minutes). Following the addition, stirring at 0° C. was continued for a further 1 hour. To the resultant suspension was added a solution of freshly prepared copper(I) chloride (12.9 g. 0.13 mol) in degassed 38% hydrochloric acid and the reaction stirred to ambient temperature over 90 minutes before heating the reaction to 70° C. to complete the decomposition of the diazonium salt. The reaction was cooled, diluted with water (750 ml) and then air was passed through the mixture for 30 minutes before adding 0.88 ammonia to ca. pH 9. The blue mixture was shaken with diethyl ether (600 ml) and any remaining solids removed by filtration. The organic layer was then washed with 5% aqueous ammonia, water, brine and dried over anhydrous sodium sulphate. This solution was filtered and then pre-adsorbed on to silica. Purification by dry flash chromatography eluting with isohexane and a gradient of ethyl acetate from 5% to 20% gave 5-bromo-2-chloro-3-nitropyridine as a pale yellow solid (13.1 g, 55%) followed by recovered starting material (6.4 g); $\delta_H$ (400 MHz, $CDCl_3$) 8.36 (1H, d, J 1, H-6), 8.69 (1H, d, J 1, H-4).

A solution of 5-bromo-2-chloro-3-nitropyridine (7.0 g, 29 mmol) and 3-(pyridin-3-yl)phenylamine (5.0 g, 29 mmol) in 1-methyl-2-pyrrolidinone (10 ml) and triethylamine (4 ml, 29 mmol) was heated at 100° C. for 90 minutes. The reaction was cooled, suspended in ethyl acetate (400 ml) and insoluble material removed by filtration. The filtrate was then washed with water, brine and dried over anhydrous sodium sulphate. This solution was filtered and pre-adsorbed on to silica gel. Purification by silica gel chromatography eluting with hexane containing triethyline (1%) on a gradient of ethyl acetate from 20% to 35% gave N-(5-bromo-3-nitropyridin-2-yl)-N-[3-(pyridin-3-yl)phenyl]amine as a red solid (5.1 g, 47%); $\delta_H$ (400 MHz, CDCl$_3$) 7.35–7.45 (2H, m, ArH), 7.51 (1H, t, J 8, ArH), 7.62 (1H, d, J 8, ArH), 7.88–7.91 (2H, m, pyridyl-H and NH), 8.53 (1H, s, pyridyl-H), 8.62 (1H, d, J 5, pyridyl-H), 8.68 (1H, s, pyridyl-H), 9.88 (1H, s, pyridyl-H), 10.14 (1H, s, pyridyl-H); m/z (ES$^+$) 371 and 373 (M$^+$+H).

A suspension of N-(5-bromo-3-nitropyridin-2-yl)-N-[3-(pyridin-3-yl)phenyl]amine (3.7 g, 10 mmol), sodium sulphide nonahydrate (7.2 g, 30 mmol) and ammonium chloride (1.6 g, 30 mmol) in methanol (15 ml) was heated under reflux for 90 minutes. The reaction was cooled, evaporated to dryness and the residue suspended in ethyl acetate (200 ml). This was washed with water, brine, dried over anhydrous sodium sulphate, filtered and evaporated to dryness to afford 5-bromo-N$^2$-[3-(pyridin-3-yl)phenyl]-pyridine-2,3-diamine as a yellow oil (3.4 g, 100%) which was used without purification; m/z (ES$^+$) 341 and 343 (M$^+$+H).

A mixture of crude 5-bromo-N$^2$-[3-(pyridin-3-yl)phenyl]pyridine-2,3-diamine and 98% formic acid was heated at 80° C. for 3 hours. The reaction was cooled, evaporated to dryness, the residue suspended in water and made basic by the cautious addition of solid sodium hydrogen carbonate. This was then extracted with ethyl acetate, the organics dried over anhydrous sodium sulphate, filtered and pre-adsorbed on to silica. Purification by silica gel chromatography eluting with dichloromethane/methanol/0.88 NH$_3$ (95:4.5:0.5) furnished 6-bromo-3-[3-(pyridin-3-yl)phenyl]-3H-imidazo[4,5-b]pyridine as a tan solid (3.1 g, 89% over 2 steps), m.p. 212–213° C. (Found C, 57.24; H, 2.98; N, 15.57. C$_{17}$H$_{11}$BrN$_4$. 0.25H$_2$O requires C, 57.40; H, 3.26; N, 15.75); $\delta_H$ (400 MHz, d$_6$-DMSO) 7.55 (1H, dd, J 5 and 5), 7.76 (1H, t, J 8), 7.86 (1H, d, J 8), 8.04 (1H, d, J 8), 8.22 (1H, d, J 8), 8.27 (1H, s), 8.56 (2H, d, J 6), 8.64 (1H, d, J 5), 9.04 (1H, s), 9.11 (1H, s); m/z (ES$^+$) 351 and 353 (M$^+$+H).

A suspension of 6-bromo-3-[3-(pyridin-3-yl)phenyl]-3H-imidazo[4,5-b]pyridine (351 mg, 1 mmol), 3-furanboronic acid (168 mg, 1.5 mmol), tetrakis(triphenylphosphine)palladium(0) (25 mg) and 1,3-propanediol (360 µl, 5 mmol) in 1,2-dimethoxyethane (6 ml) and 2M sodium carbonate solution (3 ml) was heated at 90° C. for 16 hours. The reaction was cooled and partitioned between ethyl acetate (50 ml) and water (50 ml). The organic layer was then washed with brine, dried over anhydrous sodium sulphate, filtered and pre-adsorbed on to silica. Purification by silica gel chromatography eluting with dichloromethane/methanol/0.88 NH$_3$ (95:4.5:0.5) furnished the title compound as a cream-coloured solid (208 mg, 62%), m.p. 191–192° C. (Found C, 73.13; H, 3.93; N, 16.01. C$_{21}$H$_{14}$N$_4$O. 0.4H$_2$O requires C, 72.99; H, 4.32; N, 16.21); $\delta_H$ (400 MHz, d$_6$-DMSO) 7.17 (1H, s), 7.54–7.57 (1H, m), 7.74–7.85 (3H, m), 8.09 (1H, d, J 8), 8.22 (1H, d, J 8), 8.35 (2H, d, J 6), 8.50 (1H, s), 8.63 (1H, d, J 4), 8.80 (1H, s), 9.05 (1H, s), 9.07 (1H, s); m/z (ES$^+$) 339 (M$^+$+H).

EXAMPLE 2

1-[3-(6-(Furan-3-yl)-3H-imidazo[4,5-b]pyridin-3-yl)phenyl]pyrrolidin-2-one

A suspension of 1-iodo-3-nitrobenzene (24.9 g, 0.1 mol), copper bronze (320 mg, 5 mmol) and potassium carbonate (15.2 g, 0.11 mol) in 2-pyrrolidinone was heated under a stream of nitrogen at 200° C. for 45 minutes. The reaction was cooled to ambient temperature, diluted with water (2000 ml) and extracted with diethyl ether (800 ml). The organic phase was then washed with water (2×800 ml), brine and dried over anhydrous sodium sulphate containing decolourising charcoal (2 g). Filtration and evaporation to dryness gave a yellow solid which was triturated with isohexane to give 1-(3nitrophenyl)pyrrolidin-2-one as a yellow powder (3.0 g, 15%). $\delta_H$ (360 MHz, CDCl$_3$) 2.19–2.27 (2H, m), 2.67 (2H, t, J 8), 3.94 (2H, t, J 7), 7.54 (1H, t, J 8), 8.00 (1H, ddd, J 8, 2 and 1), 8.22 (1H, ddd, J 8, 2 and 1), 8.35 (1H, t, J 2).

A suspension of 1-(3-nitrophenyl)pyrrolidin-2-one (3.0 g, 15 mmol) in ethanol (50 ml) was heated until complete solution was obtained. The solution was cooled to ambient temperature then treated with 10% palladium on charcoal (150 mg) and hydrogenated at 50 psi until hydrogen uptake ceased (ca. 2 hours). The mixture was filtered through a glass microfibre filter paper (Whatman GF/A) and evaporated to dryness to give 1-(3-aminophenyl)pyrrolidin-2-one as a pale green oil (2.6 g, 100%) which was used without purification.

A suspension of 5-bromo-2-chloro-3-nitropyridine (3.79 g, 16 mmol), 1-(3-aminophenyl)pyrrolidin-2-one (2.56 g, 15 mmol) and potassium carbonate (2.0 g, 15 mmol) in 1,2-dichloroethane (25 ml) was heated at reflux for 60 hours. The reaction was cooled, diluted with dichloromethane (200 ml) and extracted with water. The organic phase was then dried over anhydrous sodium sulphate, filtered and pre-adsorbed on to silica (25 g). Purification by column chromatography eluting with isohexane on a gradient of ethyl acetate (10%–40%) gave 1-[3-(5-bromo-3-nitropyridin-2-ylamino)phenyl]pyrrolidin-2-one as a red solid (3.7 g, 68%).

1-[3-(6-Bromo-3H-imidazo[4,5-b]pyridin-3-yl)phenyl]pyrrolidin-2-one was prepared from 1-[3-(5-bromo-3-nitropyridin-2-ylamino)phenyl]pyrrolidin-2-one as described in Example 1. Oxalate salt, white crystals, m.p. 194–195° C. (from ethanol); $\delta_H$ (360 MHz, d$_6$-DMSO) 2.10 (2H, quin, J 7), 2.56 (2H, t, J 8), 3.92 (2H, t, J 7), 7.58–7.65 (2H, m), 7.78–7.81 (1H, m), 8.19 (1H, s), 8.52–8.54 (2H, m), 8.93 (1H, s); m/z (ES$^+$) 357 and 359 (M$^+$+H).

The title compound was prepared from 1-[3-(6-bromo-3H-imidazo[4,5-b]pyridin-3-yl)phenyl]pyrrolidin-2-one as described in Example 1. Free base, yellow crystals, m.p. 208–210° C. (from ethyl acetate); $\delta_H$ (360 MHz, d$_6$-DMSO) 2.11 (2H, quin, J 7), 2.54 (2H, t, J 8), 3.93 (2H, t, J 7), 7.16 (1H, s), 7.60 (1H, t, J 8), 7.68–7.71 (1H, m), 7.78–7.81 (2H, m), 8.28 (1H, t, J 2), 8.35 (1H, s), 8.48 (1H, s), 8.76 (1H, s), 8.90 (1H, s); m/z (ES$^+$) 345 (M$^+$+H).

EXAMPLE 3

6-(Furan-3-yl)-3-[3-(imidazol-1-yl)phenyl]-3H-imidazo[4,5-b]pyridine

An intimate mixture of 1-iodo-3-nitrobenzene (24.9 g, 0.1 mol), copper bronze (320 mg, 5 mmol), potassium carbonate (15.2 g, 0.11 mol) and imidazole (15.0 g, 0.22 mol) was heated under a stream of nitrogen at 200° C. for 90 minutes. The reaction was cooled to 100° C., carefully treated with water (750 ml) and the resulting suspension stirred to ambient temperature over 16 hours. Filtration gave a grey-coloured solid which was dissolved in hot toluene (125 ml) and treated with decolourising charcoal (2 g). Filtration and cooling afforded 1-(3-nitrophenyl)-1H-imidazole as pale green needles (13.5 g, 71%). $\delta_H$ (360 MHz, CDCl$_3$) 7.29 (1H, br s), 7.38 (1H, br s), 7.68–7.78 (2H, m), 7.97 (1H, br s), 8.23–8.29 (2H, m).

A solution of 1-(3-nitrophenyl)-1H-imidazole (6.5 g, 34 mmol) in glacial acetic acid (50 ml) was treated with 10% palladium on charcoal (320 mg) and hydrogenated at 50 psi until hydrogen uptake ceased (ca. 3 hours). The mixture was filtered through a glass microfibre filter paper (Whatman GF/A) and evaporated to dryness. The residue was azeotroped twice with toluene to give 3-(imidazol-1-yl) phenylamine as a yellow oil (5.5 g, 100%) which was used without purification. m/z (ES$^+$) 360 (M$^+$+H).

A mixture of 5-bromo-2-chloro-3-nitropyridine (4.1 g, 17 mmol), 3-(imidazol-1-yl)phenylamine (2.5 g, 16 mmol) and potassium carbonate (1.3 g, 9.4 mmol) in N,N-dimethylformamide (15 ml) was heated at 110° C. for 2 hours. The reaction was cooled to ambient temperature, diluted with ethyl acetate (100 ml) and methanol (100 ml) then pre-adsorbed on to silica. Purification by silica gel chromatography eluting with dichloromethane/methanol/0.880 NH$_3$ (97:2.7:0.3) gave N-(5-bromo-3-nitropyridin-2-yl)-N-[3-(imidazol-1-yl)phenyl]amine as a red solid (1.1 g, 19%).

6-Bromo-3-[3-(imidazol-1-yl)phenyl]-3H-imidazo[4,5-b] pyridine was prepared from N-(5-bromo-3-nitropyridin-2-yl)-N-[3-(imidazol-1-yl)phenyl]amine as described in Example 1. Oxalate salt, cream-coloured powder, m.p. 236–238° C. (from ethanol); $\delta_H$ (400 MHz, d$_6$-DMSO) 7.23 (1H, s), 7.75 (2H, m), 7.92 (1H, s), 8.01–8.03 (1H, m), 8.24 (1H, s), 8.51 (1H, s), 8.57 (2H, dd, J 6 and 2), 9.09 (1H, s); m/z (ES$^+$) 340 and 342 (M$^+$+H).

The title compound was prepared from 6-bromo-3-[3-(imidazol-1-yl)phenyl]-3H-imidazo[4,5-b]pyridine as described in Example 1. Oxalate salt, cream-coloured powder, m.p. 202–204° C. (from ethanol); $\delta_H$ (400 MHz, d$_6$-DMSO) 7.16 (1H, s), 7.24 (1H, s), 7.75–7.82 (3H, m), 7.93 (1H, s), 8.07–8.12 (1H, m), 8.31 (1H, s), 8.36 (1H, s), 8.50–8.52 (2H, m), 8.80 (1H, s), 9.06 (1H, s); m/z (ES$^+$) 328 (M$^+$+H).

EXAMPLE 4

6-(Furan-3-yl)-3-[3-(morpholin-4-ylmethyl)phenyl]-3H-imidazo[4.5-b]pyridine

Anhydrous zinc chloride (15.4 g, 0.11 mol) was dissolved in methanol (250 ml) and then treated with sodium cyanoborohydride (14.2 g, 0.23 mmol). After stirring for 15 minutes at ambient temperature a further quantity of methanol (200 ml) was added giving a colourless solution of zinc cyanoborohydride together with a small quantity of solid sodium chloride.

A suspension of 3-nitrobenzaldehyde (30 g, 0.2 mol) in methanol (150 ml) was treated with morpholine and the resulting orange solution cooled to 0° C. The solution of zinc cyanoborohydride prepared above was then introduced by means of a double-ended needle and the reaction stirred to ambient temperature over 16 hours. The reaction was filtered and the filtrate evaporated to dryness. The residue was dissolved in diethyl ether (600 ml) and washed with 1N hydrochloric acid (1 l). The organic layer (containing 3-nitrobenzyl alcohol) was discarded. The aqueous layer was made basic with 4N sodium hydroxide and extracted with diethyl ether (750 ml). The organic layer was dried over anhydrous sodium sulphate, filtered and pre-adsorbed on to silica. Purification by dry flash chromatography eluting with dichloromethane/methanol/0.880 NH$_3$ (95:4.5:0.5) gave 4-(3-nitrobenzyl)morpholine as a pale yellow oil which crystallised on standing (22.2 g, 50%). $\delta_H$ (360 MHz, CDCl$_3$) 2.45–2.48 (4H, m), 3.59 (2H, s), 3.71–3.74 (4H, m), 7.49 (1H, t, J 8), 7.68 (1H, d, J 8), 8.12 (1H, d, J 8), 8.22 (1H, s).

A solution of 4-(3-nitrobenzyl)morpholine (3.0 g, 14 mmol) in ethanol (40 ml) was treated with 10% palladium on charcoal (150 mg) and hydrogenated at 50 psi until hydrogen uptake ceased (ca. 2 hours). The mixture was filtered through a glass microfibre filter paper (Whatman GF/A) and evaporated to dryness to give 3-(morpholin-4-ylmethyl) phenylamine as a colourless oil (2.6 g, 100%) which was used without purification. m/z (ES$^+$) 193 (M$^+$+H).

N-(5-Bromo-3-nitropyridin-2-yl)-N-[3-(morpholin-4-ylmethyl)phenyl]amine was prepared from 5-bromo-2-chloro-3-nitropyridine and 3-(morpholin-4-ylmethyl) phenylamine as described in Example 3.

6-Bromo-3-[3-(morpholin-4-ylmethyl)phenyl]-3H-imidazo[4,5-b]pyridine was prepared from N-(5-bromo-3-nitropyridin-2-yl)-N-[3-(morpholin-4-ylmethyl)phenyl] amine as described in Example 1. Maleate salt, cream-coloured powder, m.p. 176–178° C. (from ethyl acetate); $\delta_H$ (400 MHz, d$_6$-DMSO @ 340K) 2.64–2.68 (4H, m), 3.68–3.72 (4H, m), 4.00 (2H, s), 6.13 (2H, s), 7.51 (1H, d, J 8), 7.64 (1H, t, J 8), 7.89 (1H, d, J 8), 7.94 (1H, s), 8.47 (1H, d, J 2), 8.52 (1H, d, J 2), 8.89 (1H, s); m/z (ES$^+$) 373 and 375 (M$^+$+H).

The title compound was prepared from 6-bromo-3-[3-(morpholin-4-ylmethyl)phenyl]-3H-imidazo[4,5-b]pyridine as described in Example 1. Maleate salt, cream-coloured powder, m.p. 182–184° C. (from ethanol); $\delta_H$ (400 MHz, d$_6$-DMSO) 2.96 (4H, br s), 3.73 (4H, br s), 4.16 (2H, br s), 6.11 (2H, s), 7.17 (1H, s), 7.53 (1H, d, J 8), 7.69 (1H, t, J 8), 7.82 (1H, s), 8.00 (1H, d, J 8), 8.36 (1H, s), 8.49 (1H, d, J 2), 8.77 (1H, d, J 2), 8.92 (1H, s); m/z (ES$^+$) 361 (M$^+$+H).

EXAMPLE 5

6-Phenyl-3-[3-(pyridin-3-yl)phenyl]-3H-imidazo[4,5-b]pyridine

The title compound was prepared from 6-bromo-3-[3-(pyridin-3-yl)phenyl]-3H-imidazo[4,5-b]pyridine and phenylboronic acid as described in Example 1. Free base, white powder, m.p. 179–180° C. (from ethanol); $\delta_H$ (400 MHz, CDCl$_3$) 7.41–7.44 (1H, m), 7.52 (2H, t, J 7), 7.65–7.74 (4H, m), 7.83 (1H, d, J 8), 7.97 (1H, d, J 8), 8.07 (1H, s), 8.35 (1H, d, J 2), 8.44 (1H, s), 8.49 (1H, s), 8.65 (1H, d, J 5), 8.72 (1H, s), 8.95 (1H, s); m/z (ES$^+$) 349 (M$^+$+H).

EXAMPLE 6

1-[3'-(6-(Furan-3-yl)imidazo[4,5-b]pyridin-3-yl) biphenyl-2-yl]ethanone

A solution of 5-bromo-2-chloro-3-nitropyridine (2.37 g, 10 mmol) and m-anisidine (1.34 ml, 12 mmol) in dimethylsulphoxide (7 ml) and triethylanine (7 ml, 50 mmol) was heated at 80° C. for 3 hours. The reaction was cooled to ambient temperature then partitioned between dichloromethane and water. The organic layer was washed with water, brine, dried over anhydrous sodium sulphate, filtered and evaporated to dryness to afford a red solid. This solid was suspended in methanol (100 ml) and treated with sodium sulphide nonahydrate (9.6 g, 40 mmol) and ammonium chloride (2.14 g, 40 mmol) then heated at reflux for 3 hours. The reaction was cooled, filtered and evaporated to dryness. The resulting orange residue was suspended in 98% formic acid (40 ml) and heated at 85° C. for 12 hours. The reaction was cooled, poured into water, neutralised with 2N sodium hydroxide and the solid extracted into ethyl acetate. The organics were washed with water, brine, dried over anhydrous sodium sulphate, filtered through a pad of silica and concentrated. Trituration of the residue with 25% ether in isohexane afforded 6-bromo-3-(3-methoxyphenyl)-3H-imidazo[4,5-b]pyridine as a pale yellow solid (3.04 g, 99% over 3 steps); $\delta_H$ (400 MHz, CDCl$_3$) 3.89 (3H, s), 7.00 (1H, dd, J 8 and 2), 7.26–7.32 (2H, m), 7.48 (1H, t, J 8), 8.29 (2H, dd, J 12 and 2), 8.50 (1H, d, J 2); m/z (ES$^+$) 304 and 306 (M$^+$+H).

A suspension of 6-bromo-3-(3-methoxyphenyl)-3H-imidazo[4,5-b]pyridine (10.7 g, 35 mmol) in hydrobromic acid (80 ml of a 30 wt. % solution in acetic acid) was heated at 100° C. for 20 hours. After cooling to ambient temperature the reaction mixture was slowly dissolved in excess 3N sodium hydroxide, keeping the temperature <20° C. (to prevent hydrolysis of the benzimidazole back to the bis-amine). The aqueous phase was extracted with ether (×2) then adjusted to pH 7 with concentrated hydrochloric acid. The resulting solid was collected by filtration, washed with water and dried under high vacuum to give 3-(6-bromoimidazo[4,5-b]pyridin-3-yl)phenol as a beige-coloured solid (10.2 g, 99%); $\delta_H$ (400 MHz, d$_6$-DMSO) 6.88 (1H, ddd, J 8, 2 and 1), 7.28 (1H, ddd, J 8, 2 and 1), 7.35–7.41 (2H, m), 8.52 (2H, dd, J 11 and 2), 8.91 (1H, s), 9.96 (1H, br s); m/z (ES$^+$) 290 and 292 (M$^+$+H).

A mixture of 3-(6-bromoimidazo[4,5-b]pyridin-3-yl)phenol (2.32 g, 8 mmol), 3-furanboronic acid (1.43 g, 12.8 mmol), potassium phosphate (3.4 g, 16 mmol) and tetrakis(triphenylphosphine)palladium(0) (370 mg) in degassed N,N-dimethylformamide (12 ml) was heated at 80° C. for 20 hours. After cooling to ambient temperature the mixture was dissolved in 3N sodium hydroxide and extracted with dichloromethane, then with ether. The aqueous phase was adjusted to pH 7 with concentrated hydrochloric acid and the resulting solid collected by filtration, washed with water and dried under high vacuum to afford 3-[6-(furan-3-yl)imidazo[4,5-b]pyridin-3-yl]phenol as a cream-coloured solid (2.2 g, 99%); $\delta_H$ (400 MHz, d$_6$-DMSO) 6.86 (1H, ddd, J 8, 2 and 1), 7.15 (1H, s), 7.33–7.45 (3H, m), 7.81 (1H, s), 8.35 (1H, s), 8.46 (1H, d, J 2), 8.54 (1H, d, J 2), 8.91 (1H, s), 9.94 (1H, br s); m/z (ES$^+$) 278 (M$^+$+H).

A cooled (−10° C.) suspension of 3-[6-(furan-3-yl)imidazo[4,5-b]pyridin-3-yl]phenol (1.0 g, 3.6 mmol) in dichloromethane (15 ml) was treated with pyridine (870 μl, 11 mmol) then with trifluoromethanesulphonic anhydride (730 μl, 4.3 mmol) and stirred to ambient temperature over 30 minutes. Thin layer chromatography (3% triethylamine in ethyl acetate) indicated complete conversion to product. The reaction was partitioned between dichloromethane and 0.1N hydrochloric acid, the organics were washed with water, brine, dried over anhydrous sodium sulphate, filtered and evaporated to give trifluoromethanesulphonic acid 3-[6-(furan-3-yl)imidazo[4,5-b]pyridin-3-yl]phenyl ester as a brown solid (1.5 g, 100%). Used without further purification; m/z (ES$^+$) 410 (M$^+$+H).

A mixture of trifluoromethanesulphonic acid 3-[6-(furan-3-yl)imidazo[4,5-b]pyridin-3-yl]phenyl ester (123 mg, 0.3 mmol), 2-acetylphenylboronic acid (100 mg, 0.6 mmol), potassium phosphate (127 mg, 0.6 mmol), tris(dibenzylideneacetone)dipalladium(0) (8 mg) and 2,2'-bis(diphenylphosphino)-1,1'-binaphthyl (11 mg) in degassed N,N-dimethylacetamide (1.5 ml) was heated at 80° C. for 16 hours. The reaction was cooled then partitioned between dichloromethane and water. The organic phase was washed with brine, dried over anhydrous sodium sulphate, filtered and concentrated in vacuo. The residue was dissolved in methanol (2 ml) and the resulting dark solution loaded onto an SCX ion-exchange cartridge and washed with methanol (2×6 ml). The crude product was then eluted using concentrated ammonia in methanol (7 ml of 10% solution). The basic fraction was concentrated to dryness and the residue purified by HPLC eluting with acetonitrile and water containing 0.1% trifluoroacetic acid. The appropriate fractions were freeze-dried to furnish the trifluoroacetate salt of the title compound as a white powder (30 mg); $\delta_H$ (400 MHz, d$_6$-DMSO) 2.38 (3H, s), 7.21 (1H, dd, J 2 and 1), 7.15 (1H, dt, J 8 and 1), 7.58–7.62 (2H, m), 7.68–7.78 (3H, m), 7.86 (1H, t, J 2), 8.08–8.09 (2H, m), 8.47 (1H, d, J 2), 8.55 (1H, d, J 2), 8.77 (1H, s), 9.07 (1H, s), m/z (ES$^+$) 380 (M$^+$+H).

EXAMPLE 7

3'-[6-(Furan-3-yl)imidazo[4,5-b]pyridin-3-yl]biphenyl-2-carbaldehyde

The title compound was prepared from trifluoromethanesulphonic acid 3-[6-(furan-3-yl)imidazo[4,5-b]pyridin-3-yl]phenyl ester and 2-formylphenylboronic acid as described in Example 6. Trifluoroacetate salt (cream-coloured powder): $\delta_H$ (400 MHz, d$_6$-DMSO) 7.10–7.11 (1H, m), 7.49 (1H, dt, J 8 and 1), 7.59–7.62 (2H, m), 7.70 (1H, t, J 8), 7.75–7.79 (2H, m), 7.93–7.95 (1H, m), 8.08–8.11 (2H, m), 8.33–8.34 (1H, m), 8.48 (1H, d, J 2), 8.76 (1H, d, J 2), 8.99 (1H, s), 9.99 (1H, s); m/z (ES$^+$) 366 (M$^+$+H).

EXAMPLE 8

3'-[6-(Furan-3-yl)imidazo[4,5-b]pyridin-3-yl]biphenyl-2-carbonitrile

A degassed mixture of trifluoromethanesulphonic acid 3-[6-(furan-3-yl)imidazo[4,5-b]pyridin-3-yl]phenyl ester (82 mg, 0.2 mmol), potassium acetate (60 mg, 0.6 mmol), bis(pinacolato)diboron (60 mg, 0.24 mmol), 1,1'-bis(diphenylphosphino)ferrocene (6 mg) and dichloro[1,1'-bis(diphenylphosphino)ferrocene]palladium(II) dichloromethane adduct (9 mg) in 1,4-dioxane (3.5 ml) was heated at 80° C. for 16 hours. On cooling, the reaction mixture was diluted with ethyl acetate (30 ml) and filtered. The filtrate was washed with water, brine, dried over anhydrous sodium sulphate, filtered through a pad of Florisil and evaporated to dryness to afford 6-(furan-3-yl)-3-[3-(4,4,5,5-tetramethyl-[1,3,2]dioxaborolan-2-yl)-phenyl]-3H-imidazo[4,5-b]pyridine as a red-brown oil (85 mg). This was used without further purification; m/z (ES$^+$) 388 (M$^+$+H).

A degassed mixture of crude 6-(furan-3-yl)-3-[3-(4,4,5,5-tetramethyl-[1,3,2]dioxaborolan-2-yl)phenyl]-3H-imidazo[4,5-b]pyridine (85 mg), 2-bromobenzonitrile (54 mg, 0.3 mmol), tetrakis(triphenylphosphine)palladium(0) (10 mg) and potassium phosphate (85 mg, 0.4 mmol) in N,N-dimethylformamide (1.5 ml) was heated at 80° C. for 16 hours. The reaction was cooled to ambient temperature, diluted with dichloromethane (10 ml) and methanol (10 ml) and pre-adsorbed onto silica. Purification by silica gel chromatography eluting with dichloromethane/methanol/concentrated ammonia (96:3.5:0.5) furnished the title compound as a cream-coloured solid (31 mg). This was converted to its oxalate salt and crystallised from hot ethanol; $\delta_H$ (400 MHz, d$_6$-DMSO) 7.16–7.17 (1H, m), 7.66 (1H, td, J 8 and 1), 7.70–7.72 (1H, m), 7.78–7.81 (3H, m), 7.87 (1H, td, J 8 and 1), 8.02 (1H, dd, J 8 and 1), 8.17–8.19 (1H, m), 8.25–8.26 (1H, m), 8.36 (1H, s), 8.51 (1H, d, J 2), 8.78 (1H, d, J 2), 9.02 (1H, s); m/z (ES$^+$) 363 (M$^+$+H).

EXAMPLE 9

3-[3-(6(Furan-3-yl)imidazo[4,5-b]pyridin-3-yl)phenyl]thiophene-2-carbonitrile

The title compound was prepared from 6-(furan-3-yl)-3-[3-(4,4,5,5-tetramethyl-[1,3,2]dioxaborolan-2-yl)phenyl]-

3H-imidazo[4,5-b]pyridine and 3-bromothiophene-2-carbonitrile as described in Example 8 to afford the free base as a tan sold; δ$_H$ (400 MHz, d$_6$-DMSO) 7.17 (1H, s), 7.70 (1H, d, J 5), 7.78–7.86 (3H, m), 8.15 (1H, d, J 8), 8.20 (1H, d, J 5), 8.36–8.37 (2H, m), 8.50 (1H, d, J 2), 8.78 (1H, d, J 2), 9.02 (1H, s); m/z (ES$^+$) 369 (M$^+$+H).

What is claimed is:

1. A compound of formula I, or a pharmaceutically acceptable salt or a prodrug thereof:

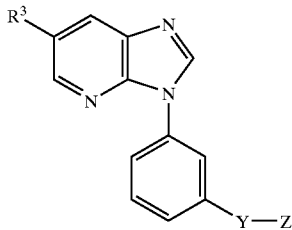

wherein

Y represents a chemical bond, or a methylene (CH$_2$), carbonyl (C=O), thiocarbonyl (C=S) or amide (CONH or NHCO) linkage;

Z represents an optionally substituted phenyl, heteroaryl or heteroaryl(C$_{1-6}$)alkyl group, wherein heteroaryl is selected from the group consisting of pyridine, pyrrolidine, imidazole and thiophene, or a group of formula —NR$^1$R$^2$;

R$^1$ and R$^2$ independently represent hydrogen, hydrocarbon or a heterocyclic group wherein the heterocyclic group is selected from the group consisting of pyridine, pyrrolidine, imidazole and thiophene; or R$^1$ and R$^2$, together with the intervening nitrogen atom, represent an optionally substituted heterocyclic ring selected from azetidinyl, pyrrolidinyl, piperidinyl, piperazinyl, morpholinyl and thiomorpholinyl; and R$^3$ represents phenyl or furanyl, which groups may be optionally substituted.

2. The compound of claim 1 represented by formula II, or a pharmaceutically acceptable salt or a prodrug thereof:

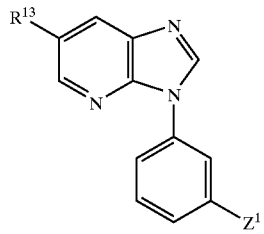

wherein

Z$^1$ represents an optionally substituted aryl or heteroaryl group, wherein heteroaryl is selected from the group consisting of pyridine, pyrrolidine, imidazole and thiophene; and R$^{13}$ represents phenyl or furanyl.

3. The compound of claim 2 wherein Z$^1$ represents cyanophenyl, formylphenyl, acetylphenyl, pyridinyl, cyanothienyl or imidazolyl.

4. A compound of claim 2 wherein R$^{13}$ represents phenyl or furanyl.

5. A compound which is selected from:

6-(furan-3-yl)-3-[3-(pyridin-3-yl)phenyl]-3H-imidazo[4,5-b]pyridine;
1-[3-(6-(furan-3-yl)-3H-imidazo[4,5-b]pyridin-3-yl)phenyl]pyrrolidin-2-one;
6-(furan-3-yl)-3-[3-(imidazol-1-yl)phenyl]-3H-imidazo[4,5-b]pyridine;
6-phenyl-3-[3-(pyridin-3-yl)phenyl]-3H-imidazo[4,5-b]pyridine;

or a pharmaceutically acceptable salt or a prodrug thereof.

6. A compound which is selected from:

1-[3'-(6-(furan-3-yl)imidazo[4,5-b]pyridin-3-yl)biphenyl-2-yl]ethanone;
3'-[6-(furan-3-yl)imidazo[4,5-b]pyridin-3-yl]biphenyl-2-carbaldehyde;
3'-[6-(furan-3-yl)imidazo[4,5-b]pyridin-3-yl]biphenyl-2-carbonitrile;
3-[3-(6-(furan-3-yl)imidazo[4,5-b]pyridin-3-yl)phenyl]thiophene-2-carbonitrile;

or a pharmaceutically acceptable salt or a prodrug thereof.

7. A pharmaceutical composition comprising a compound of claim 1 or a pharmaceutically acceptable salt or a prodrug thereof and a pharmaceutically acceptable carrier.

8. A process for the preparation of the compound of claim 1, which comprises:

(A) reacting a compound of formula III:

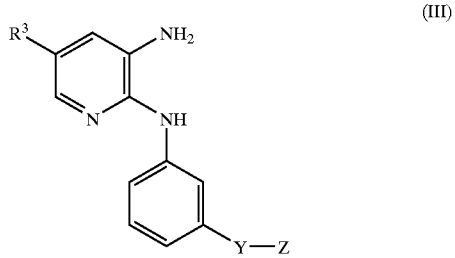

wherein Y, Z and R$^3$ are as defined in claim 1; with formic acid; or (B) reacting a compound of formula VI with a compound of formula VII:

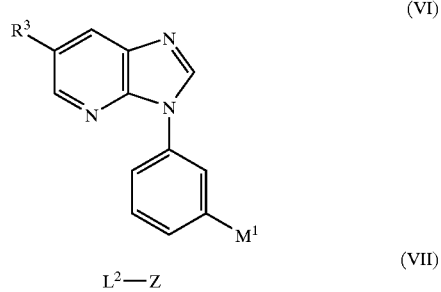

wherein Z and R$^3$ are as defined in claim 1, L$^2$ represents a suitable leaving group, and M$^1$ represents a boronic acid moiety —B(OH)$_2$ or a cyclic ester thereof formed with an organic diol; in the presence of a transition metal catalyst; or (C) reacting a compound of formula VIII with a compound of formula IX:

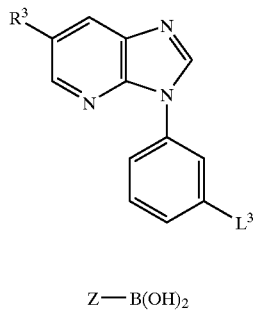
(VIII)

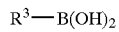
(IX)

wherein Z and $R^3$ are as defined in claim 1, and $L^3$ represents a suitable leaving group; in the presence of a transition metal catalyst; or (D) reacting a compound of formula X with a compound of formula XI:

$R^3$—B(OH)$_2$        (X)

-continued

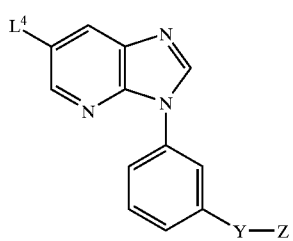
(XI)

wherein Y, Z and $R^3$ are as defined in claim 1, and $L^4$ represents a suitable leaving group; in the presence of a transition metal catalyst.

9. A method for the treatment of anxiety which comprises administering to a patient in need of such treatment an effective amount of the compound of claim 1 or a pharmaceutically acceptable salt or a prodrug thereof.

10. A method for the prevention of anxiety which comprises administering to a patient in need of such prevention an effective amount of the compound of claim 1 or a pharmaceutically acceptable salt or a prodrug thereof.

* * * * *